United States Patent
Schmidt et al.

(10) Patent No.: US 9,267,101 B2
(45) Date of Patent: Feb. 23, 2016

(54) CELL CULTURE INSERT

(75) Inventors: Timo Schmidt, Stuttgart (DE); Lothar Just, Hechingen (DE); Holger Becker, Pfungstadt (DE)

(73) Assignee: NATURIN VISCOFAN GMBH, Weinheim (DE)

( * ) Notice: Subject to any disclaimer, the term of this patent is extended or adjusted under 35 U.S.C. 154(b) by 15 days.

(21) Appl. No.: 13/878,143

(22) PCT Filed: Oct. 8, 2010

(86) PCT No.: PCT/EP2010/065100
§ 371 (c)(1),
(2), (4) Date: Jun. 20, 2013

(87) PCT Pub. No.: WO2012/045368
PCT Pub. Date: Apr. 12, 2012

(65) Prior Publication Data
US 2013/0267019 A1    Oct. 10, 2013

(51) Int. Cl.
C12M 1/12 (2006.01)
C12M 1/32 (2006.01)
C12M 3/00 (2006.01)
C12M 1/42 (2006.01)

(52) U.S. Cl.
CPC .............. *C12M 25/04* (2013.01); *C12M 23/12* (2013.01); *C12M 23/44* (2013.01); *C12M 25/14* (2013.01); *C12M 35/08* (2013.01)

(58) Field of Classification Search
CPC ...... C12M 23/12; C12M 23/44; C12M 35/08; C12M 25/04; C12M 25/14
See application file for complete search history.

(56) References Cited

U.S. PATENT DOCUMENTS

| | | | |
|---|---|---|---|
| 5,409,829 A | 4/1995 | Mussi | |
| 5,470,743 A | 11/1995 | Mussi | |
| 5,534,227 A * | 7/1996 | Lahm et al. | 422/536 |
| 5,665,596 A | 9/1997 | Mussi | |
| 5,759,851 A | 6/1998 | Mathus | |
| 2008/0076170 A1* | 3/2008 | Annala et al. | 435/297.4 |
| 2010/0190197 A1 | 7/2010 | Martin et al. | |

OTHER PUBLICATIONS

Office Action issued in European Patent Application 10 770 754.9 dated Sep. 3, 2015.
PCT/EP2010/065100 International Search Report and Written Opinion, Aug. 5, 2014.

* cited by examiner

*Primary Examiner* — Gautam Prakash
(74) *Attorney, Agent, or Firm* — Notaro, Michalos & Zaccaria P.C.

(57) ABSTRACT

A cell culture device allows co-cultivation on both sides of a membrane and has an outer tubular body with upper end having an opening and lower end closed by the membrane, an inner surface and an outer surface, which can be colonized with biological material, a complementary tubular body whose inner diameter fits onto the outer diameter of the lower end and a hanger component with upper end and a lower end. A flange extends from the upper end and the outer diameter component fits the inner diameter of the outer tubular body. The outer tubular body in a first step is connected to the complementary tubular body to form a standing insert for a first cell cultivation, and in a second step wherein the outer tubular body is disengaged from the complementary tubular body and is attached to the hanger component for a second cell cultivation.

12 Claims, 10 Drawing Sheets

CELL CULTURE INSERT

TECHNICAL FIELD OF THE INVENTION

The present invention has application in the field of cell and tissue culture techniques.

BACKGROUND OF THE INVENTION

Cell culture inserts have become a valuable tool in cell biology as they promote growth and differentiation of a variety of cell types. Cell culture inserts can be used to investigate transport, diffusion, uptake, metabolization and secretion of both synthetic and natural compounds. Furthermore, inserts allow the cultivation of complex three-dimensional tissue.

Apart from the scientific value of studying tissue growth and organization in vitro in biological studies, such tissues are of major importance for the development of in vitro assays to assess toxicity and pharmacokinetic parameters of chemicals, cosmetics and pharmaceutical substances.

With this, the number of animal experiments which are performed to assess such parameters can be significantly reduced. Moreover, the use of human cells and tissue cultivated in cell culture inserts yields much more significant results and reduces the rate of "false positives" i.e. the rate of compounds defined as safe or positive but where a correlation of animal and human data is not possible. Often such false positives are identified only late in drug development or even in clinical trials causing high investments which have to be written off.

Inserts typically consist of a hollow body, closed at one end with a membrane, on which the cells are grown. The membranes are either permeable or, if impermeable, contain microperforations to ensure transport of nutrients across the membrane. The insert is positioned into the well of a cell culture plate in a way that the membrane is in contact with the cell culture medium, either submerged or at the media/air interface.

Cells are usually seeded on the side of the membrane which is showing away from the well of the plate. To allow free diffusion of the cell culture medium, such inserts are positioned into the well plate standing on small feet thus creating a space between the lower part of the insert and the bottom of the well plate. Alternatively, a hanging device can be used, having flanges protruding sideways from the upper part of the insert structure.

The possibility to culture cells on both sides of the insert membrane has gained more attention during the recent years. Cell-to-cell communication across the insert membrane, chemotaxis and other cell migration phenomena can be studied. Electrophysiological analyses are possible on either side of the insert membrane. Apical and basolateral regions of polarized cells can be investigated separately. Stem cells can be separated from feeder cells by cultivation on both sides of the membrane. However, the types of inserts specifically developed for such applications are difficult to use and show significant disadvantages in their practical handling in the cell culture laboratory.

One such insert structure is disclosed in U.S. Pat. No. 5,470,743A. This document describes an assembly consisting of an inverted standard insert on which a support device is positioned. Both support device and insert are connected via a gasket which leaves an inner space consisting of the outer surface of the membrane of the inverted insert on which cells can be grown. After successful cultivation, the assembly is taken apart and the insert with the cells cultivated on the outer surface of the membrane can be hanged into the well of a cell culture plate. Subsequently, cells can be cultured on the inner surface of the membrane. The assembly has to be protected against contamination by a sealing on its upper and lower end. Furthermore, this document discloses a gasket comprising a double sided adhesive to keep support device and insert closely connected during the initial cell culture step. This is a major disadvantage for the disassembly of the parts as there is the risk that the membrane and/or the cells will be damaged during this step. Moreover, the assembly can be used only as a stand-alone device, not in connection with cell culture plates impairing an effective handling especially when many of such cultures are performed at the same time.

Another solution for cell cultivation on both sides of the membrane of an insert is provided in U.S. Pat. No. 5,759,851A. This document describes a movable frame which is placed inside a cylindrical body. A precise positioning of said movable frame within the tubular structure is possible e.g. by using a jig having a flange at one end which exceeds the diameter of the tubular body. The movable frame carries a membrane for the cultivation of biological material. Cultivation on both sides of the membrane is possible by inverting the cylindrical body. To avoid leakage of cell culture medium, the movable frame bears a sealing around its outer diameter. This solution has the disadvantage that a separate tool is needed for height adjustment of the movable frame. Another disadvantage is that it is mandatory to have a firm rim structure or border upon which the jig exerts its action and which, at the same time, serves as a carrier for the membrane. If cells are seeded on such a structure, they grow either on the free, non-supported membrane or on the membrane supported by the rim structure or, in the worst case, on the rim structure itself. Another structure which will come in unwanted direct contact with cells and the culture medium is the sealing of the movable frame. It is obvious that the growth conditions on these different surfaces deviate substantially. Both the movable frame and the sealing ring are artificial materials which influence cell growth, cell proliferation and/or cell differentiation. It can also not be guaranteed that the sealing ring between the frame and the inner wall of the cylindrical body is leak-proof especially when it is shifted by the jig. All these factors make a safe and easy handling difficult and obviate many possible applications.

U.S. Pat. No. 5,759,851A further describes a solution to suppress the formation of air bubbles in the standing insert. This is achieved by forming the end of the movable frame which is pointing towards the bottom of the well plate in a shallow angle. The user then has to carefully lower the device at a defined angle into the cell culture medium and watch for air bubble entrapment. This angular form obviously requires a broader frame; the free-standing part of the membrane which can be used for cell culture is significantly reduced. Furthermore, the handling is difficult. Finally, in most cases inserts are formed in a way that their outer walls fit with minimal distance to the wall of the cell culture plate. It is obvious that the use of a frame with shallow angles is only possible in a well plate which has a very large inner diameter compared to the outer diameter of the insert. Only in this case it is possible to tilt the insert in a way that the angle of the frame and the level of the medium are the same and no air is entrapped.

DESCRIPTION OF THE INVENTION

It is an object of the present invention to provide a device, i. e. an insert assembly or structure, which allows the co-cultivation on both sides of a membrane of said insert assembly or structure and which overcomes the difficulties and disadvantages in handling of those co-culture inserts described in the art.

This is achieved by means of the present invention which refers to a multifunctional cell culture device which comprises multiple elements which can be combined in specific ways, as described below, to allow the safe and effective co-culturing of cells on both sides of the membrane.

The cell culture device according to the present invention comprises, in its minimum configuration, the following elements:

An outer tubular body having an upper end and a lower end. The upper end comprises an opening; the lower end is closed by a membrane which can be colonized with biological material. This membrane has an inner surface and an outer surface, with regard to the outer tubular body.

A complementary tubular body, having an upper end and a lower end, the inner diameter of said complementary tubular body fitting, in whole or partly, onto the outer diameter of the lower end of the outer tubular body.

A hanger component having an upper end and a lower end. From the upper end extend sideways at least one flange. The outer diameter of this hanger component fits, in whole or partly, into the inner diameter of the outer tubular body. Thus, this hanger component, when connected to the outer tubular body as described before, results in a hanging insert structure. The one or more lateral flanges serve as supporting elements, fixing the upper end of the hanger component at the rim of the well.

For a first step of cell cultivation on one side of the membrane the outer tubular body is inverted and the complementary tubular body is connected to the lower end of the outer tubular body in a way that results in a standing insert with the complementary tubular body forming a cell cultivation chamber. Cells can then be seeded onto the outer surface of the membrane which projects into the complementary tubular body.

After an appropriate cultivation period, for a second step the ensemble of outer tubular body and complementary tubular body is turned around. The hanger component is then connected to the outer tubular body. Thereafter, the complementary tubular body is removed. The resulting hanging insert is placed into the well of a cell culture plate. The outer surface of the membrane onto which the cells were seeded in the first step is now facing the bottom of the cell culture well. The second cell seeding is now performed by using the upward projecting inner surface of the membrane.

The development of air bubbles under the outer surface of the membrane is prevented by disconnecting the complementary tubular body. The resulting hanging insert does not provide any structures which would entrap such air bubbles and thus prevents the above-mentioned problem.

Moreover, both the standing insert structure for the first cultivation step and the hanging insert structure for the second cultivation step fit into standard wells of commercially available cell culture plates. The handling steps are easy to perform and give a maximum level of safety with regard to air bubble entrapment, sterility and the drying-out of the first cell culture.

The individual elements of the cultivation device according to the present invention can be further described in preferred embodiments which in no way shall limit the foregoing general description and general applicability of the co-culture device.

PREFERRED EMBODIMENT OF THE INVENTION

Figure 1:
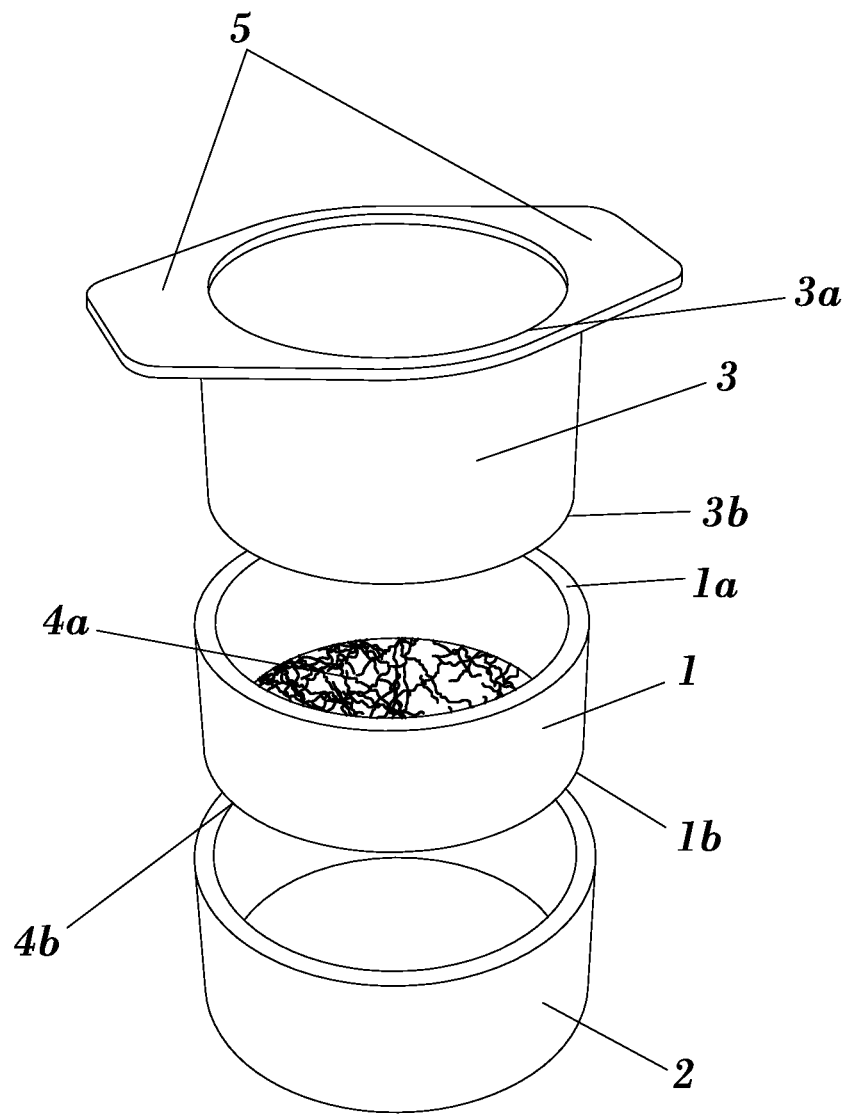
FIG. 1.—Shows a schematic perspective view of the cell culture device according to the present invention, wherein the outer tubular body, the complementary tubular body and the hanger component can be appreciated.

At sight of the figures, a preferred embodiment of the cell culture device of the invention comprises:

An outer tubular body (1) having an upper end (1a) and a lower end (1b). The upper end (1a) comprises an opening; the lower end (1b) is closed by a membrane (4) which can be colonized with biological material. This membrane (4) has an inner surface (4a) and an outer surface (4b), with regard to the outer tubular body (1).

A complementary tubular body (2), having an upper end and a lower end, the inner diameter of said complementary tubular body (2) fitting, in whole or partly, onto the outer diameter of the lower end (1b) of the outer tubular body (1).

A hanger component (3) having an upper end (3a) and a lower end (3b). From the upper end (3a) extend sideways one or more flanges (5). The outer diameter of this hanger component (3) fits, in whole or partly, into the inner diameter of the outer tubular body (1). Thus, this hanger component (3) when connected to the outer tubular body (1) as described before, forms a hanging insert structure.

Figure 2:
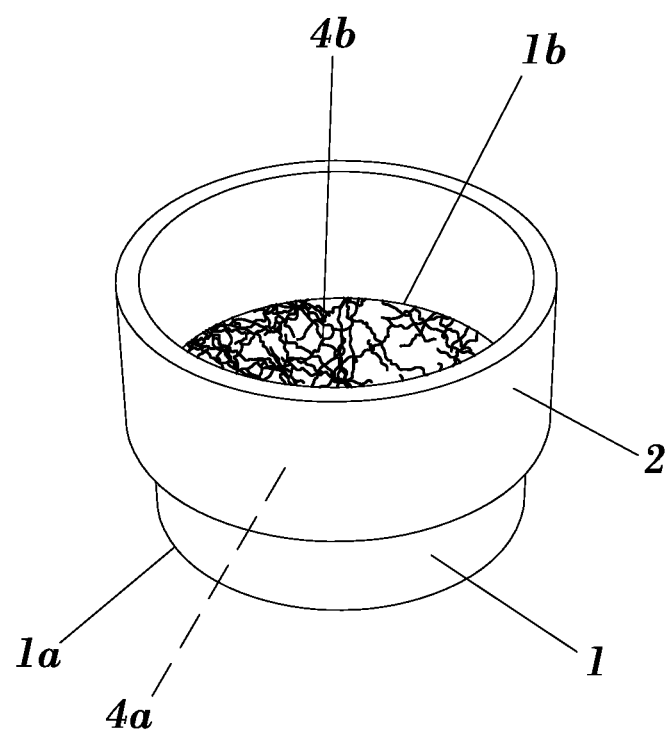
FIG. 2.—Shows a schematic perspective view of a first step of cell cultivation on one side of the membrane, wherein the outer tubular body is inverted and the complementary tubular body is connected to the lower end of the outer tubular body.

Firstly, as shown in FIG. 2, for cell cultivation on one side of the membrane (4), the outer tubular body (1) is inverted and the complementary tubular body (2) is connected to the lower end (1b) of the outer tubular body (1) in a way that results in a standing insert with the complementary tubular body (2) and the membrane (4) forming a cell cultivation chamber.

Cells can then be seeded onto the outer surface (4b) of the membrane (4) which projects into the complementary tubular body (2).

Figure 3A:
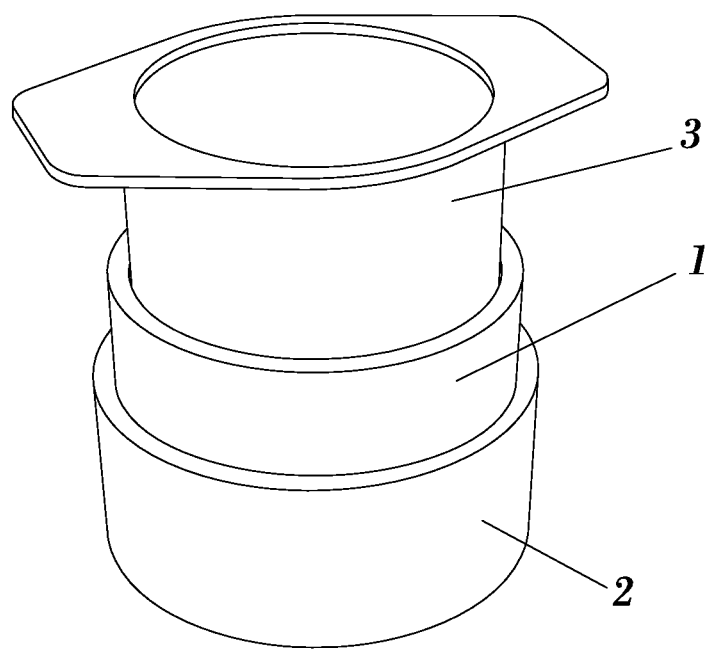
FIG. 3.—Shows two schematic views of a second step of cell cultivation, view a showing the ensemble of outer tubular body and complementary tubular body being turned around and the hanger component being connected to the outer tubular body; and thereinafter, view b showing a cross section of the complementary tubular body being removed and the resulting hanging insert being placed into the well of a cell culture plate.
Figure 3B:
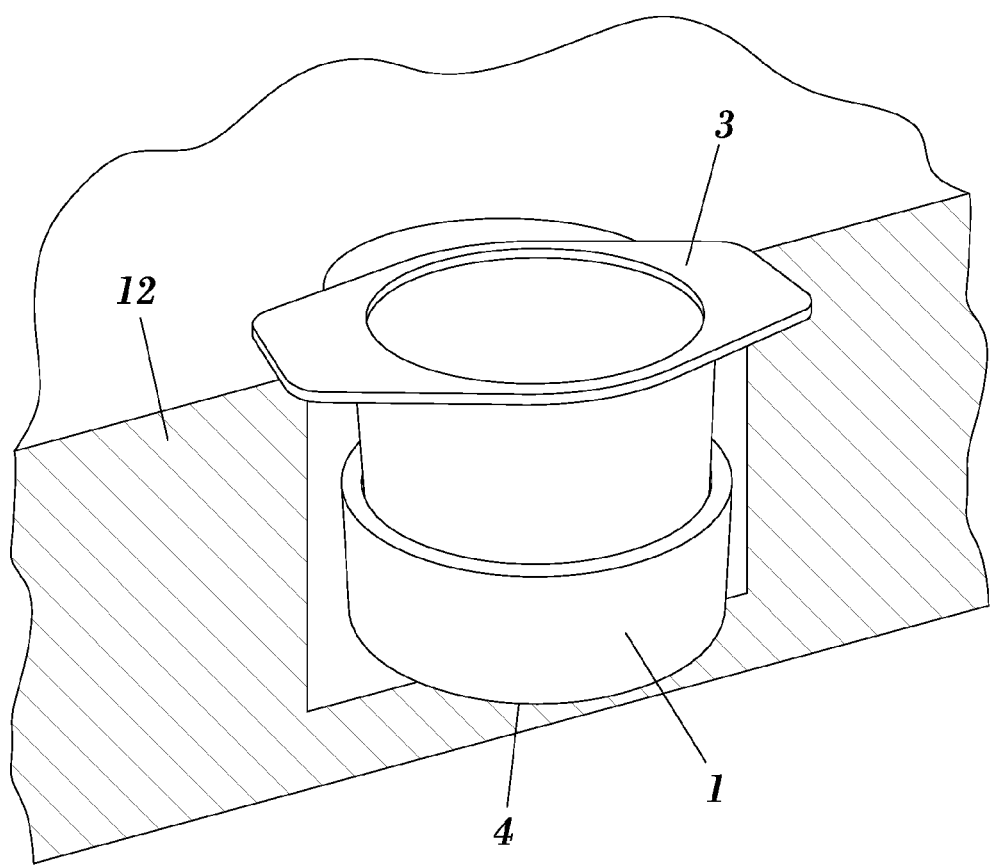

Secondly, after an appropriate cultivation period, the ensemble of outer tubular body (1) and complementary tubular body (2) is turned around, as shown in FIG. 3a. The hanger component (3) is then connected to the outer tubular body (1). Thereafter, the complementary tubular body (2) is removed. The resulting hanging insert, shown in FIG. 3b, is placed into the well (12) of a cell culture plate. The outer surface (4b) of the membrane (4) onto which the cells were seeded in the first step is now facing the bottom of the cell culture well (12). The second cell seeding is now performed by using the upward projecting inner surface (4a) of the membrane (4).

The development of air bubbles under the outer surface (4b) of the membrane (4) is prevented by disconnecting the complementary tubular body (2). The resulting hanging insert does not provide any structures which would entrap such air bubbles and thus prevents the above-mentioned problem.

Moreover, both the standing insert structure for the first cultivation step, shown in FIG. 2, and the hanging insert structure for the second cultivation step, shown in FIG. 3b, fit into standard wells (12) of commercially available cell culture plates. The handling steps are easy to perform and give a maximum level of safety with regard to air bubble entrapment, sterility and the drying-out of the first cell culture.

The individual elements of the cultivation device according to the present invention can be further described in preferred embodiments which in no way shall limit the foregoing general description and general applicability of the co-culture device.

Figure 4A:
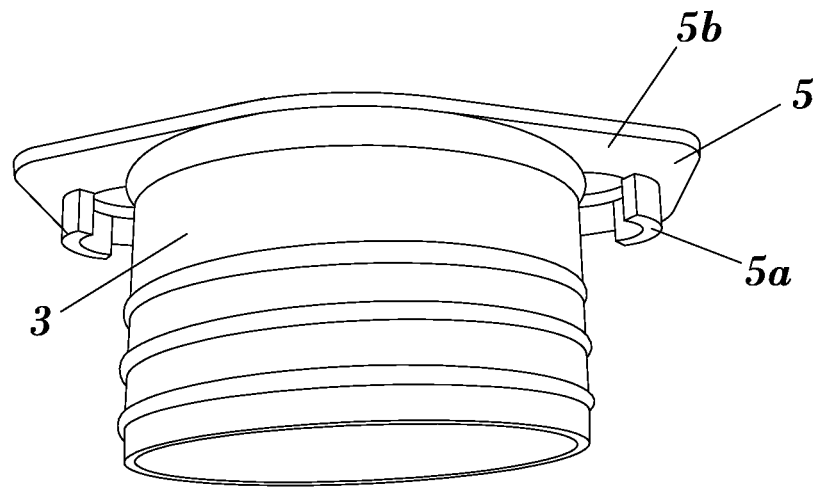
FIG. 4.—Shows three schematic perspective views corresponding to three embodiments of the hanger component, all of them having flanges at their upper end and notches on their outer surface, wherein said notches consist of parallel ridges, according to the embodiment shown in FIG. 4a, consisting in turn of two perspective views; a screw-like structure, shown in FIG. 4b; and a step-like structure, as shown in FIG. 4c.
Figure 4A:
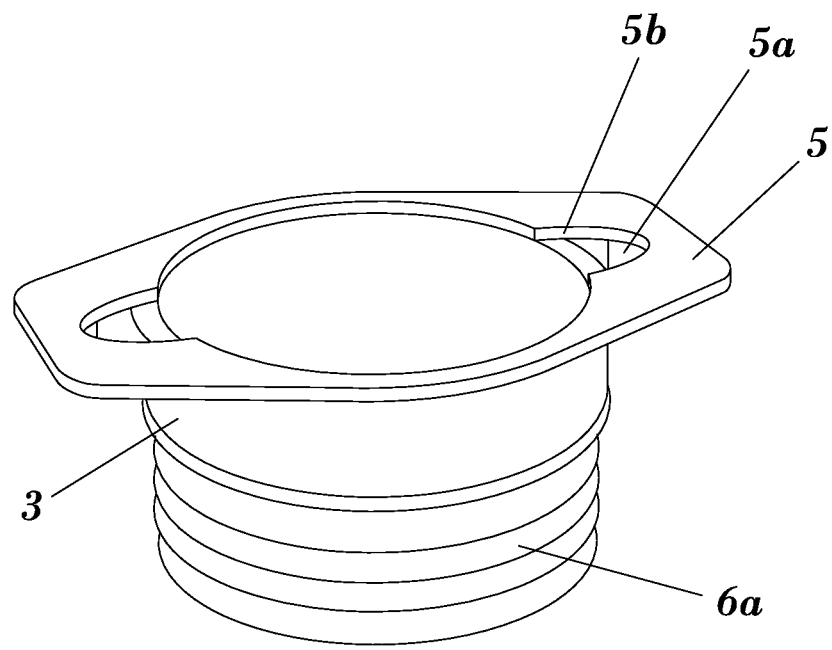
Figure 4B:
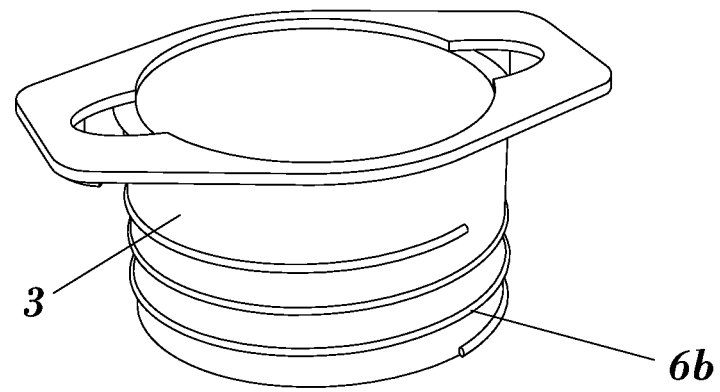
Figure 4C:
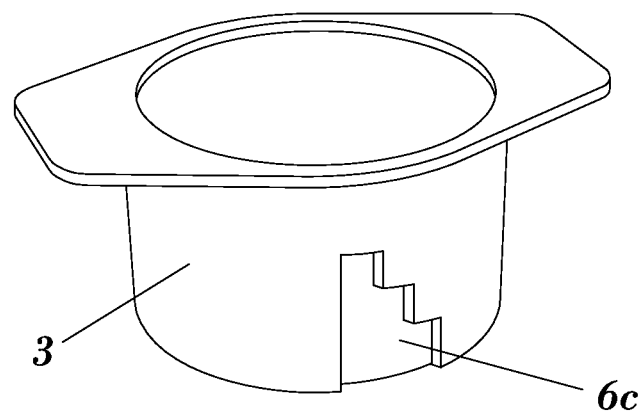

The hanger component (3) in its preferred form, as shown in FIG. 4a, has an upper end (3a) bearing one or more flanges (5) which extend sideways from the tubular body of said hanger component (3). Said flanges (5) optionally have openings (5a) which permit the insertion of pointed tools like a forceps for easy taking of the insert, or the tip of a pipette to add e. g. substances to the cultivation medium, and allow additionally gas exchange with the environment. Furthermore they comprise a distance holder (5b) which allows the precise central positioning of the hanger component (3) in the well (12) of a cell culture plate. The hanger component (3) further may comprise notches (6a, 6b, 6c) on its outer surface. Said notches may form parallel ridges (6a), screw-like notches (6b), as shown in FIG. 4b, or, in a most preferred embodiment of the invention shown in FIG. 4c, step-like notches (6c).

The outer tubular body (1), in its preferred form, has an upper end (1a) which bears one or more protrusions extending laterally into the inside of this outer tubular body (1). These protrusions are complementary to and fit into the notches (6a, 6b, 6c) on the outer surface of the hanger component (3). The protrusions are appropriate to engage or fit with each kind of notches (6a, 6b, 6c). Regarding the particular embodiments of the hanger component (3) shown in FIGS. 4a and 4b, the corresponding outer tubular body (1) bears protrusions extending along the whole upper end (1a) of said outer tubular body (1), thus forming complementary structures to each of the parallel ridges (6a) and screw-like notches (6b).

Figure 5:
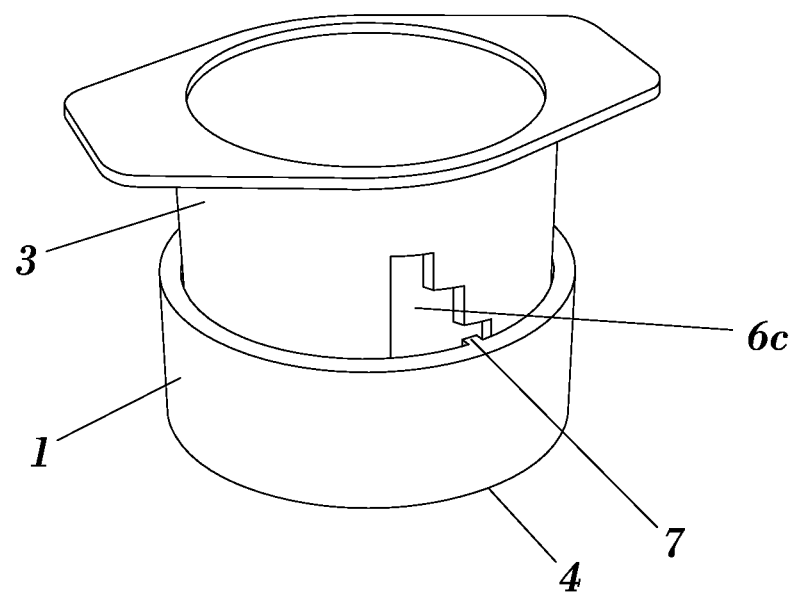
FIG. 5.—Shows a schematic perspective view of the assembly between the hanger component embodiment shown in FIG. 4c and the outer tubular body.

According to another embodiment, shown in FIG. 5, the upper end (1a) of the outer tubular body (1) comprises lateral protrusions (7) extending laterally into the inside of the outer tubular body (1), which match and extend into the step-like notches (6c) of the hanger component (3). The outer tubular body (1) and the hanger component (3) can thus be easily assembled.

The distance between membrane (4) of the hanging insert and the bottom of the well (12) plate can thus be adjusted either continuously using the outer tubular body (1) and the hanger component (3) which are designed in a way that they can be pressed or screwed together. Otherwise, as shown in FIG. 5, using step-like notches (6c) and appropriate lateral protrusions (7) of the outer tubular body (1), the distance can be adjusted in discrete steps.

The diameter of the outer surface of the hanger component (3) and the diameter of the inner surface of the outer tubular body (1) can be designed in a way that the friction between these elements provides a leak-proof connection. This ensures that there is no leakage of cell culture medium or contamination of the medium on the one side of the membrane (4) by medium from the other side of the membrane (4).

Figure 6:
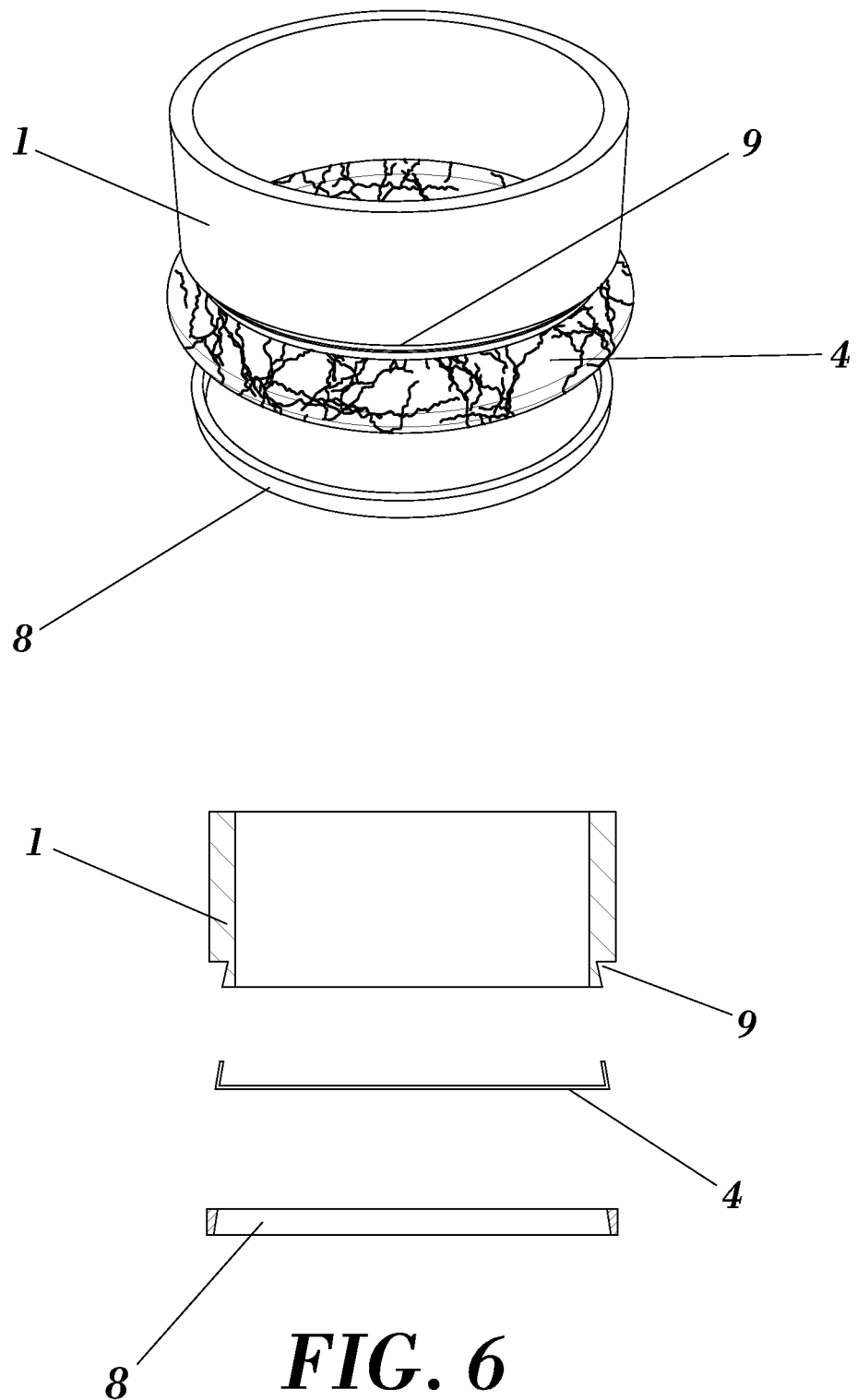
FIG. 6.—Shows a schematic perspective view and a cross section thereof wherein an embodiment of the outer tubular body according to the invention is shown, and wherein the membrane is adhered to the bottom of the outer tubular body by means of a clamping ring.

The membrane (4) of the present invention may be adhered to the lower end (1b) of the outer tubular body (1) by various means which are known to those skilled in the art, e.g. by heat sealing. Preferred is the use of a clamping ring (8), as shown in FIG. 6, which fits to the ring structure of the lower end (1b) of the outer tubular body (1), smoothly adhering to the outer surface of said outer tubular body (1). Most preferred the lower end (1b) of the outer tubular body (1) comprises an undercut (9) configured to tightly house the clamping ring (8), wherein the membrane (4) remains fixed between said clamping ring (8) and said undercut (9). In a most preferred embodiment, this clamping ring (8) can be removed. This allows the release of the membrane (4) with attached co-cultured cells from the insert structure. The membrane/cell structure can then be used for further studies, e.g. for histology, microscopy or as an implant.

It is obvious for a person skilled in the art that, depending on the type of membrane (4) and its characteristics, especially its wall thickness, the inner diameter of the clamping ring (8) and the precise dimensions of the undercut (9) have to be adjusted to achieve a correct and tight insertion of the membrane (4) into the insert structure, i. e. at the outer tubular body (1).

Figure 7:
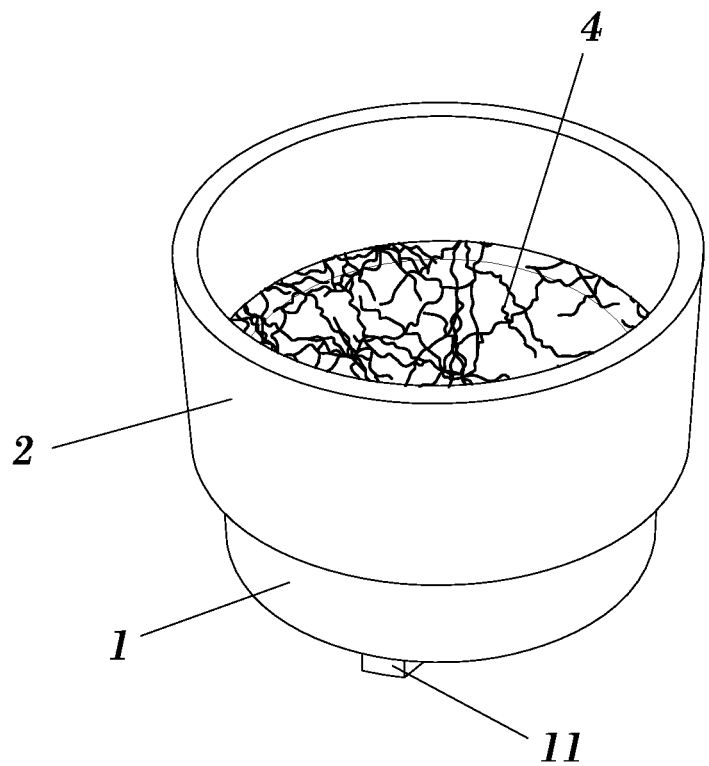
FIG. 7.—Shows a schematic perspective view and a cross section of the complementary tubular body that comprises in its inner diameter and at its lower end, at least a segment or stopper area which is narrower than the outer diameter of the outer tubular body which has three feet at its lower end.
Figure 7:
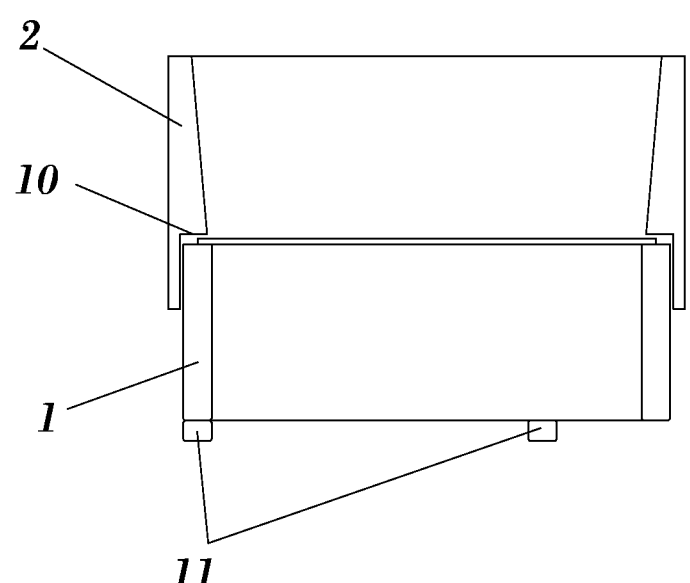

According to a preferred embodiment of the invention, the complementary tubular body (2) comprises, in its inner diameter and at one end, a stopper area (10) which is narrower than the outer diameter of the outer tubular body (1). Upon assembly of such a complementary tubular body (2) and the outer tubular body (1), as shown in FIG. 7, said outer tubular body (1) can thus be fixed in a definite position within the complementary tubular body (2). The outer tubular body (1) may comprise further at least one, preferably three, protrusions (11) at its upper end (1a) which may act as feet, spacing away the upper end (1a) of the outer tubular body (1) from the bottom of the well (12) of a cell culture plate.

A person skilled in the art will understand that the elements comprising the outer tubular body (1), the complementary tubular body (2) and the hanger component (3), and also the clamping ring (8) may be produced by molding, preferably by injection molding, from medical grade plastic or comparable material which does not transmit any foreign substances harmful to cell culture. A variety of materials is available for this purpose, including, but not limited to, polystyrene, polyethylene terephthalate, polycarbonate, silicone, polypropylene or polyethylene.

The membrane (4) which is fitted to the outer tubular body (1), preferably by means of a clamping ring (8), can be made essentially of any synthetic or natural material. Examples of such materials include, but are not limited to polyethylene terephthalate, polycarbonate, alginate, chitosan, poly lactide, poly glycolide, poly lactic acid, collagen or compositions thereof. Such membranes (4) may be characterized by a compact but permeable structure or they may contain pores, preferentially of a defined size and arranged in defined density, to allow the exchange of nutrients and chemical signals across the membrane. It is also applicable to use membranes (4) which are coated on one or on both surfaces, e.g. with a collagen solution.

Figure 8:
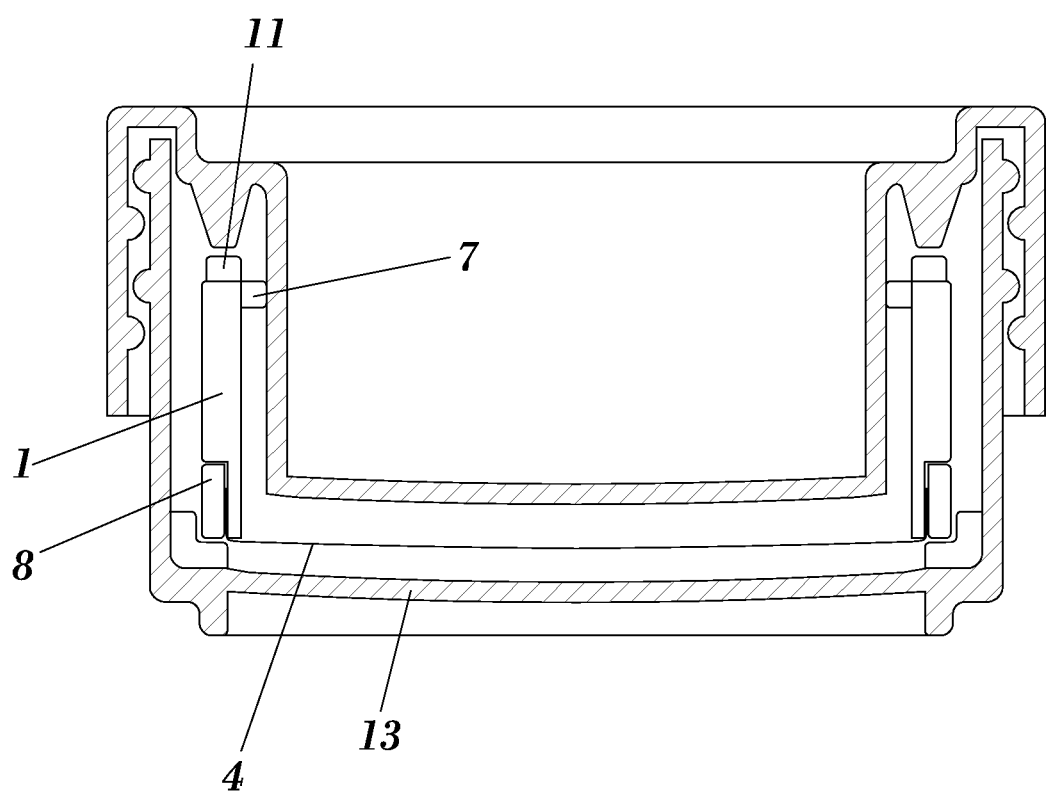
FIG. 8.—Shows a cross section of the outer tubular body placed inside a cryo-preservation container.

Furthermore, FIG. 8 shows a particular use of the device, wherein the outer tubular body (1) is placed inside a cryopreservation container (13). The lateral protrusions (7) at the upper end (1a) of the outer tubular body (1) and pointing to the inside, keep a cap element of a cryo-container (13) at a defined distance to the device of the invention. In combination with spacers attached to the cryo-container (13), this provides a constant cover of the membrane with attached cells with freezing media. In this embodiment of the invention, the outer tubular body (1) carries additionally protrusions (11) which show away from its upper end (1a). These upward protrusions (11) of the outer tubular body (1) provide in this device an air trap to avoid air enclosure at cell level. The elasticity of the membrane (4) allows a downward bending forced by the curvature of the cryo-container (13). Due to this bending entrapped air aside the biological material is squeezed towards the air trap. After freezing, the outer tubular body (1) and the biological material attached to the membrane (4) can be thawed rapidly due to the thin and constant cover of freezing media aside the outer tubular body (1) and the membrane (4). Large ice agglomerations delaying the thaw process are avoided. The outer tubular body (1) can be taken out of the cryo-container (13) by connecting it with the hanger component (3) and transferred to a standard well (12) of a cell culture plate to free the biological material from freezing media and for further cultivation.

The invention claimed is:

1. A cell culture device comprising:
   an outer tubular body (1) having an upper end (1a) and a lower end (1b), the upper end (1a) comprising an opening and the lower end (1b) being closed by a membrane (4), the membrane having an inner surface (4a) and an outer surface (4b) which can both be colonized with biological material,
   characterized in that the cell culture device further comprises:
   a complementary tubular body (2), whose inner diameter fits, at least partly, onto the outer diameter of the lower end (1b) of the outer tubular body (1), and
   a hanger component (3) having an upper end (3a), a lower end (3b), an axial passage there through, and an outer surface; wherein the axial passage is open at least at the lower end (3b) of the hanger component (3); wherein at least one flange (5) extends sideways from the upper end (3a) of the hanger component (3); wherein at least part of the outer surface of the lower end (3b) of the hanger component (3) has a shape complimentary to an inner surface of the outer tubular body (1), and wherein the lower end (3b) of the hanger component and the inner surface of the outer tubular body (1) collectively form a connection means adapted to reversibly axially connect the hanger component (3) and the tubular body (1);
   wherein said outer tubular body (1) is shaped for reversible connection to the complementary tubular body (2) to form a standing insert for a first cell cultivation, and
   wherein the hanger component (3), through said connection means, is able to fully support the tubular body (1) in a position hanging below the hanger component (3) for a second cell cultivation.

2. The cell culture device of claim 1, wherein the connection means comprises one or more circumferential parallel ridges (6a) on the lower end (3b) of the hanger component which are complimentary to and fit into the inner surface of the outer tubular body (1) for reversible axial connection therewith.

3. The cell culture device of claim 1, wherein the connection means comprises screw-like threading.

4. The cell culture device of claim 1,
   wherein said connection means comprises a friction connection between the hanger component (3) and the tubular body (1); and
   wherein said outer surface of the lower end (3b) of the hanger component (3) comprises step-like notches (6c) which are complimentary to one or more protrusions on the outer tubular body (1).

5. The cell culture device of claim 1, the cell culture device being positioned within a cell culture plate, the cell culture plate comprising a top surface and one or more concave wells extending downward from the top surface, the wells each having a bottom surface;
   wherein the outer tubular body (1) and at least part of the hanger component (3) are positioned within a well of the cell culture plate; wherein said one or more flanges (5) of the hanger component (3) are positioned on the top surface of the cell culture plate and support the hanger component thereon.

6. The cell culture device of claim 5, wherein both the inner surface (4a) and the outer surface (4b) of the membrane (4) support living biological material.

7. The cell culture device of claim 1, wherein said at least one flange (5) of the hanger component (3) has an opening (5a), through which fits a pointed tool.

8. The cell culture device of claim 1, wherein said at least one flange (5) of the hanger component (3) has a distance holder (5b) which allows precise central positioning of the hanger component (3) into a well (12) of a cell culture plate.

9. The cell culture device of claim 1, wherein the upper end (1a) of the outer tubular body (1) comprises one or more lateral protrusions (7) which match and extend into one or more notches of the hanger component (3), thus allowing the distance between the membrane (4) and a bottom of a well (12) of a cell culture plate to be adjusted.

10. The cell culture device of claim 1, further comprising a clamping ring (8) which fits onto the lower end (1b) of the outer tubular body (1), and is thereby adapted for reversably adhering to the outer surface of said outer tubular body (1); wherein the lower end (1b) of the outer tubular body (1) comprises an undercut (9) configured to tightly house the clamping ring (8); and wherein the membrane (4) remains fixed between the clamping ring (8) and the undercut (9).

11. The cell culture device of claim 1, wherein one end of the complementary tubular body (2) comprises, in its inner diameter, a stopper area (10) which is narrower than an outer diameter of the outer tubular body (1).

12. The cell culture device of claim 1, wherein the outer tubular body (1) comprises a plurality of protrusions (11) at its upper end (1a) which can act as feet supporting at least the outer tubular body.

* * * * *